United States Patent [19]

Treder, Jr.

[11] 4,445,360
[45] May 1, 1984

[54] METHOD FOR ULTRASONICALLY DETERMINING CHARACTERISTICS OF A BODY

[75] Inventor: Ralph A. Treder, Jr., Ewing, N.J.

[73] Assignee: Western Electric Co., Inc., New York, N.Y.

[21] Appl. No.: 364,564

[22] Filed: Apr. 1, 1982

[51] Int. Cl.³ .................................................. G01N 29/04
[52] U.S. Cl. ........................................ 73/1 DV; 73/588
[58] Field of Search ............. 73/1 DV, 600, 599, 588, 73/290 V, 644; 310/334, 335, 336; 367/151, 13

[56] References Cited

U.S. PATENT DOCUMENTS

| | | | |
|---|---|---|---|
| 2,612,772 | 10/1952 | McConnel | 73/600 X |
| 3,394,589 | 7/1968 | Tomiska | 73/270 V |
| 3,733,889 | 5/1973 | Proctor, Jr. | 73/588 X |
| 3,832,889 | 9/1974 | Bauer | 310/336 X |
| 4,173,139 | 11/1979 | Conn | 73/1 DV |
| 4,238,963 | 12/1980 | Ries et al. | 73/644 |
| 4,287,766 | 9/1981 | Ensminger | 73/582 |

FOREIGN PATENT DOCUMENTS

| | | | |
|---|---|---|---|
| 2814336 | 5/1979 | Fed. Rep. of Germany | 73/1 DV |
| 430318 | 5/1975 | U.S.S.R. | 73/1 DV |
| 657338 | 4/1979 | U.S.S.R. | 73/644 |

Primary Examiner—Gerald Goldberg
Assistant Examiner—Tom Noland
Attorney, Agent, or Firm—M. M. de Picciotto

[57] ABSTRACT

An ultrasonic technique for remotely inspecting a body is described. A transducer (14), capable of generating and detecting ultrasonic signals, is coupled to the body. An ultrasonic signal ($A_o$) is launched by the transducer (14) into the body (e.g. 10, 11) and is reflected by any imperfection (e.g. 12) therein. The effects of variations of the transmission coefficient between the transducer and the body are substantially eliminated by intentionally cutting a predetermined calibration notch (22) into the body under test. The analysis of the reflected ultrasonic signals at the notch (22) and at any imperfection (e.g. 12) within the body gives an indication of the quality of the body independently of the transducer/body transmission coefficient.

1 Claim, 2 Drawing Figures

METHOD FOR ULTRASONICALLY DETERMINING CHARACTERISTICS OF A BODY

TECHNICAL FIELD

The present invention relates to a method for ultrasonically determining characteristics of a body and more particularly to a method for remotely inspecting joints between two metallic bodies using ultrasonics.

BACKGROUND OF THE INVENTION

Ultrasonic nondestructive techniques are well known as a tool for evaluating and analyzing physical characteristics and properties of bodies. Such known ultrasonic inspecting techniques use an ultrasonic transducer coupled to the body under test for transmitting ultrasonic signals thereinto. Any internal defect, crack, or other discontinuity within the body will reflect a portion of the ultrasonic signals back toward a receiving transducer. The time interval between the launching of the ultrasonic signals into the body and the reception of the reflected signals indicates the location of an acoustic impedance change within the body.

In order to achieve a uniform acoustical coupling between the transducer and the body under test, it has been suggested to acoustically couple the transducer to the body by means of a suitable coupling fluid. One such known technique, which requires immersion of the body and the transducer in the coupling fluid does effect uniform application of the signals into and out of the body but does not have repeatable ultrasonic transmission coefficients between the transducer and the body. It is often impractical, if not impossible, to immerse the body under test especially when such a body is an intrinsic part of a somewhat larger apparatus or arrangement.

Instead of using immersion, coupling to the body under test can be achieved by using a thin layer of a bonding agent to improve the transmission coefficient at the transducer/body interface. The bonding agent may permanently affix the transducer to the body, or it may temporarily provide coupling between the transducer and the body under test. The coupling resulting from such a thin bonding layer, is generally not accurately reproducible. Furthermore, such coupling, which is usually unmeasurable, leads to ambiguities in the values of the transmission coefficient and in the interpretation of returning echoes.

Therefore, there exists a need for a reliable and reproducible nondestructive method for ultrasonically inspecting certain characteristics of a body independently of the transmission coefficient between the transducer and the body for any given measurement.

SUMMARY OF THE INVENTION

The present invention solves the foregoing problems with a method for inspecting a body comprising the steps of coupling an ultrasonic transducer to the body, forming a predetermined calibration notch into the body at a predetermined distance from the transducer, generating ultrasonic signals into the body by means of the ultrasonic transducer, detecting first ultrasonic signals reflected by the predetermined calibration notch, detecting second ultrasonic signals reflected by any imperfection within the body, and comparing the first and second detected signals thereby determining the quality of the body independently of the transmission coefficient between the ultrasonic transducer and the body.

In accordance with another embodiment of the invention, a method for inspecting a joint between a first and a second body comprises the steps of coupling an ultrasonic transducer to one of the two bodies, forming a predetermined calibration notch into one of the two bodies at a predetermined distance from the transducer, generating ultrasonic signals into the bodies by means of the ultrasonic transducer, detecting first ultrasonic signals reflected by the predetermined calibration notch, detecting second ultrasonic signals reflected by the joint, and comparing the first and second detected signals thereby determining the quality of the joint independently of the transmission coefficient between the ultrasonic transducer and the bodies.

In a specific embodiment of the invention, a method for remotely inspecting a brazed joint between a first elongated metal electrode and a second elongated metal electrode comprises the steps of generating ultrasonic signals into the metal electrodes by means of an ultrasonic transducer directly in contact with the first metal electrode, forming a predetermined calibration notch into the first metal electrode at a predetermined distance from the transducer, detecting first ultrasonic signals reflected by the predetermined calibration notch, detecting second ultrasonic signals reflected by the joint, and comparing the first and second detected signals thereby determining the quality of the joint independently of the transmission coefficient at the interface of the ultrasonic transducer and the first electrode.

One advantage of the present invention is the ability to inspect a body without requiring its immersion in a fluid.

Another advantage of the present invention is the ability to achieve a reliable and reproducible nondestructive evaluation of the quality of a joint between two bodies.

A further advantage of the present invention is the substantial elimination of any uncertainties resulting from the coupling of an ultrasonic transducer to a body to be inspected.

A still further advantage of the present invention is its capability of remotely sensing the quality of a brazed joint between two electrodes, such joint being located in an inaccessible portion of an electrical apparatus.

These and other advantages of this invention will appear more fully upon consideration of the illustrative embodiments now to be described in detail in connection with the accompanying drawings.

DETAILED DESCRIPTION

Figure 1:
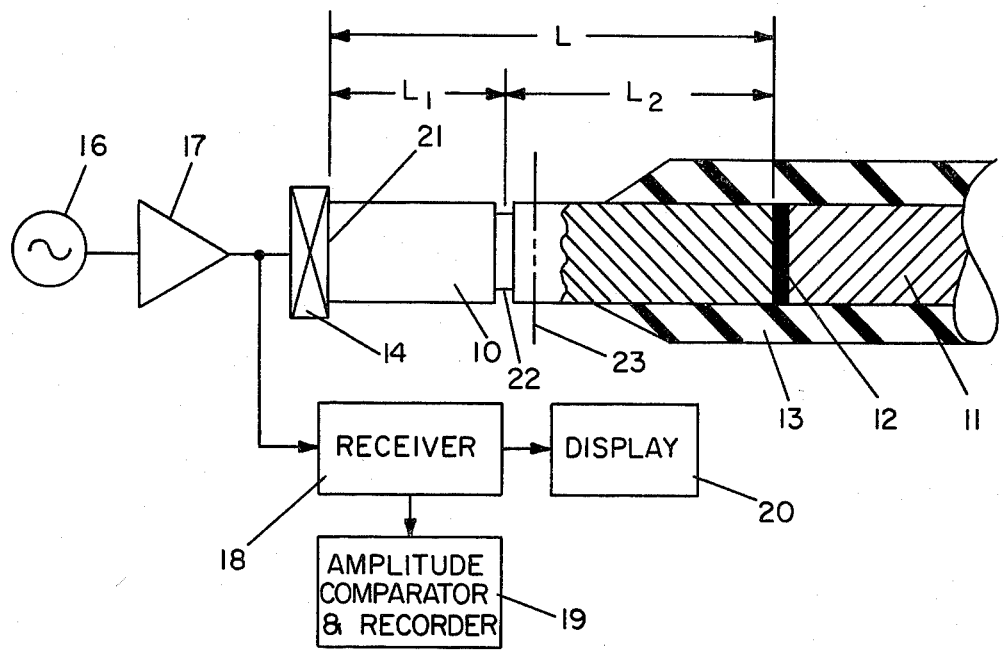
FIG. 1 is a partial cross-sectional schematic representation of an arrangement for inspecting joints in accordance with one illustrative embodiment of the present invention.

Schematically shown in FIG. 1 is an arrangement for implementing an inspection method in accordance with an illustrative embodiment of the present invention. Although such illustrative embodiment relates to a technique for inspecting a joint between two bodies, it is well within the spirit and scope of the present invention to apply the inventive concepts disclosed herein to a method for inspecting a single body. In other words, the various principles to be described hereafter are readily applicable to the inspection and detection of flaws, discontinuities, imperfections or other internal defects within a single body under test.

Shown in FIG. 1 is a first body 10 joined to a second body 11 by means of a joint 12. When inspecting a single body, the first and second bodies 10 and 11 should be viewed as the single body under test while joint 12 may be a flaw, discontinuity or imperfection within such a single body. For purpose of illustration only, the following description refers to a joint 12 between a first electrode body 10 and a second electrode body 11. However, without departing from the spirit and scope of the present invention, the present inventive concepts are also applicable to other types of bodies as well as to various types of joining or welding techniques and configurations. Electrodes 10 and 11 may, for example, be part of an electrical or electronic apparatus (not shown) wherein it is imperative to achieve a good quality joint 12 in order to increase the reliability and life of such apparatus. Furthermore, joint 12 is usually in a non accessible location within the apparatus rendering impractical a direct visual inspection of the joint or an X-ray examination thereof. A portion of electrode 10, joint 12, and electrode 11 may be encapsulated in a sealant 13, e.g., polyethelene, to protect the electrical apparatus from corrosion or other deleterious factors.

In accordance with this embodiment, electrode 10 has an initial overall length, L, larger than the required length for an output connection lead of the apparatus. Illustratively, electrodes 10 and 11 may be made of copper and may each have a diameter of the order of 0.110". Also, a small piece of well known brazing alloy of 0.110" in diameter and approximately 0.005" in thickness may be used to join the two copper electrodes. A required length for an output lead of the apparatus is typically of the order of 8". In other words, the initial overall length L of electrode 10 is larger than 8".

The determination of the quality of joint 12 is achieved by means of an ultrasonic testing technique. An ultrasonic transducer 14 is acoustically coupled to one end of electrode 10, the other end of which is joined to electrode 11 via brazed joint 12. Although transducer 14 is shown in direct contact with one end of electrode 10, other acoustic coupling techniques could be used without departing from the spirit and scope of the present invention. For example, a thin bonding layer or a coupling fluid medium may be interposed between the ultrasonic transducer 14 and one end of electrode 10 to achieve such acoustic coupling. A signal generator 16 is coupled to transducer 14 via a commercially available gating modulator and amplifier 17. The ultrasonic transducer 14 launches ultrasonic signals into the electrodes 10 and 11. Also coupled to transducer 14 is a broadband receiver 18 adapted to receive any reflected signals, or returning echo, resulting from the interaction of the launched ultrasonic signals with any defects or flaws within electrodes 10 and 11. Moreover, signals reflected at the joint 12 are also received by transducer 14 and coupled to the receiver 18. An automatic attenuation comparator and recorder 19 (for example, of a commercially available type such as a Model 2470A manufactured and sold by Matec Inc., Warwick, RI) and a display device 20 are connected to the receiver 18 for identifying the quality of the joint 12 as will be explained hereafter.

The coupling of transducer 14 to electrode 10 introduces a transmission coefficient, $T_{te}$, for the transducer/electrode interface 21. Such transmission coefficient $T_{te}$, which is a function of the change in acoustic impedance across the interface 21, varies each time a transducer (such as 14) is coupled to an electrode under test. Therefore, a determination of $T_{te}$ seems necessary each time a joint is analyzed, since variations in $T_{te}$ may exist.

In accordance with an embodiment of the present invention, the quality of joint 12 is determined independently of the transmission coefficient $T_{te}$ at the interface 21 such that echoes received at transducer 14 can be unambiguously interpreted. This is achieved by forming a predetermined calibration notch 22 into the first electrode 10 at a predetermined distance $L_1$ from transducer 14. Such a predetermined calibration notch 22 exhibits predetermined wave reflection and wave transmission characteristics depending upon the size of the notch, i.e., its width and its depth. Also, as shown in FIG. 1, a preferred calibration notch 22 is formed substantially along the periphery of the first electrode 10.

Let us assume that transducer 14 launches into the electrode 10 an ultrasonic signal having an amplitude $A_o$. Such a signal travels a length $L_1$ within electrode 10 until it encounters calibration notch 22. A portion of such signal is reflected by the notch and sent back towards transducer 14. Such reflected ultrasonic signal or returning echo signal is detected at transducer 14 and has an intensity $I_n$ given by:

$$I_n = \tfrac{1}{2}\rho c \omega^2 A_n^2 \qquad (1)$$

wherein,
 $\rho$ = electrode density,
 c = speed of sound within the electrode,
 $\omega$ = angular ultrasonic frequency, and
 $A_n$ = amplitude of the notch echo signal.
The amplitude of the notch echo signal is given by:

$$A_n^2 = A_o^2 T_{te} e^{-2\alpha L_1} R_n e^{-2\alpha L_1} T_{te} \qquad (2)$$

wherein,
 $A_o$ = amplitude of original signal launched by the ultrasonic transducer,
 $T_{te}$ = transmission coefficient of transducer/electrode interface,
 $\alpha$ = attenuation coefficient of the electrode material,
 $L_1$ = distance between the transducer and the calibration notch, and
 $R_n$ = reflection coefficient of the calibration notch.
Equation (2) can be rewritten as:

$$A_n = A_o T_{te} \sqrt{R_n}\; e^{-2\alpha L_1} \qquad (3)$$

A portion of the launched ultrasonic signal reaching notch 22 is transmitted by such notch and travels a length $L_2$ within electrode 10 until it encounters joint 12. Depending upon the quality of joint 12, such a signal can be totally reflected, partially reflected or totally transmitted by joint 12 if the latter is respectively a totally broken, partially broken or a good joint. In other words, broken joints produce relatively strong returning echoes while good joints generate negligible returning echoes. A returning echo, caused by a reflection at joint 12, reaches transducer 14 with an intensity $I_j$ given by:

$$I_j = \tfrac{1}{2}\rho c \omega^2 A_j^2 \qquad (4)$$

where $A_j$ is the amplitude of the echo signal received from the joint.

The amplitude of the joint echo signal is given by:

$$A_j^2 = (A_o^2 \, T_{te} \, e^{-2\alpha L_1} \, T_n \, e^{-2\alpha L_2}) \qquad (5)$$
$$(R_j \, e^{-2\alpha L_2} \, T_n \, e^{-2\alpha L_1} \, T_{te})$$

wherein, $T_n$ = transmission coefficient of the calibration notch, which coefficient is equal to $1-R_n$, since $R_n + T_n = 1$, $L_2$ = distance between the calibration notch and the joint, and $R_j$ = reflection coefficient of the joint.

Equation (5) can be rewritten as:

$$A_j = A_o \, T_{te} \, T_n \sqrt{R_j} \, e^{-2\alpha(L_1+L_2)} \qquad (6)$$

The combination of equations 3 and 6 yields:

$$\frac{A_j}{A_n} = \frac{\sqrt{R_j} \, T_n e^{-2\alpha L_2}}{\sqrt{1-T_n}} \qquad (7)$$

In the illustrative embodiment shown in FIG. 1, receiver 18 and amplitude comparator and recorder 19 enable the determination of the ratio of $A_j$ to $A_n$. As shown in equation 7, such a ratio is a function of $R_j$, $T_n$, $\alpha$ and $L_2$. Since $\alpha$ and $L_2$ are known, the reflection coefficient $R_j$ of the joint, and in turn the quality of such joint, may be determined independently of $T_{te}$ if $T_n$ is known.

Depending upon the material of the body under test and upon the frequency of the ultrasonic signals launched into the body, different predetermined calibration notches may be used. Prior to inspecting the body, a determination of the transmission coefficient $T_n$ of the calibration notch to be used should be made. Such a determination may be made, for example, by selecting a suitable representative sample of the body having a totally reflective reference surface thereon and by inserting the calibration notch to be used between the totally reflective reference surface and a source of ultrasonic signals. The echo signals reflected by the notch within the sample can be analyzed to determine the transmission coefficient $T_n$ by using equation 7 wherein $\alpha$, $L_2$, and the ratio $(A_j/A_n)$ are either known or measured, and $R_j = 1$ because the reference surface is totally reflective.

After determining the quality of joint 12, electrode 10 may be severed along the schematic reference line 23 thereby leaving the apparatus with an output connection lead of any desired length.

Figure 2:
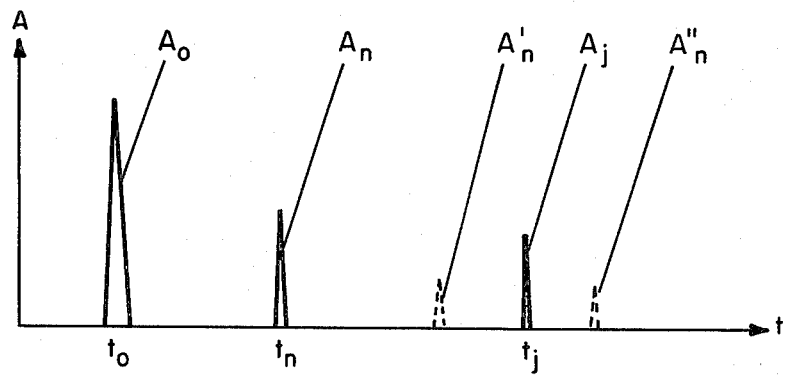
FIG. 2 is a wave diagram relating to the embodiment shown in FIG. 1.

Shown in FIG. 2 is an illustrative rectified pulse diagram of the initial ultrasonic signal ($A_o$) launched at time $t_o$ by transducer 14, the notch-reflected signal ($A_n$) as received by transducer 14, and the joint-reflected signal ($A_j$) as received by the transducer 14. Other detected signals, $A_n'$ and $A_n''$, may exist. These would correspond to possible reverberation echoes from repeated reflections of sound energy back and forth between the notch and the transducer/electrode interface. The notch-reflected signal, $A_n$, is shown at time $t_n$ which corresponds to twice the sound wave propagation time for a distance of $L_1$. Similarly, the joint-reflected signal, $A_j$, is shown at time $t_j$ which corresponds to twice the sound wave propagation time for a distance of L. The values of $t_n$ and $t_j$ will determine the appropriate gating times for comparing $A_j$ and $A_n$.

An analysis of the quality of a joint would first comprise the selection of a predetermined calibration notch having a known reflection coefficient, $R_n$, and a known transmission coefficient, $T_n$. Next, the above referenced propagation times $t_n$ and $t_j$ are determined depending upon the material of the electrodes under test and the respective wave propagation distances. As mentioned above, the propagation times $t_n$ and $t_j$ give an indication as to the expected timing of the notch-reflected echo signal, $A_n$, and the joint-reflected echo signal, $A_j$, respectively. The comparison of $A_n$ and $A_j$, e.g., the measurement of the ratio $A_j/A_n$, solves the left hand portion of equation 7. Since $\alpha$, $L_2$ and $T_n$ are known, the reflection coefficient of the joint, $R_j$, can be derived from equation 7 thus characterizing the quality of the joint.

The foregoing illustrative embodiment has been presented merely to illustrate the pertinent inventive concepts. Numerous modifications can be made by those skilled in the art without departing from the spirit and scope of the invention.

What is claimed is:

1. A method for remotely inspecting a brazed joint between a first elongated metal electrode and a second elongated metal electrode comprising the steps of:

generating ultrasonic signals into the metal electrodes by means of an ultrasonic transducer directly in contact with the first metal electrode;

forming a predetermined calibration notch substantially along the periphery of the first metal electrode at a predetermined distance from said transducer;

detecting two echo signals emanating from the electrodes, said echo signals consisting of a first ultrasonic signal reflected by said predetermined calibration notch and a second ultrasonic signal reflected by said joint; and comparing said first and second detected signals thereby determining the quality of said joint independently of the transmission coefficient at the interface of the ultrasonic transducer and the first electrode.

* * * * *